(12) United States Patent
Fleig

(10) Patent No.: US 11,869,216 B2
(45) Date of Patent: Jan. 9, 2024

(54) REGISTRATION OF AN ANATOMICAL BODY PART BY DETECTING A FINGER POSE

(71) Applicant: Brainlab AG, Munich (DE)

(72) Inventor: Oliver Fleig, Baldham (DE)

(73) Assignee: Brainlab AG, Munich (DE)

( * ) Notice: Subject to any disclaimer, the term of this patent is extended or adjusted under 35 U.S.C. 154(b) by 555 days.

(21) Appl. No.: 17/050,049

(22) PCT Filed: Jun. 13, 2019

(86) PCT No.: PCT/EP2019/065553
§ 371 (c)(1),
(2) Date: Oct. 23, 2020

(87) PCT Pub. No.: WO2019/238851
PCT Pub. Date: Dec. 19, 2019

(65) Prior Publication Data
US 2021/0074021 A1    Mar. 11, 2021

(30) Foreign Application Priority Data

Jun. 14, 2018 (WO) .................. PCT/EP2018/065746

(51) Int. Cl.
*G06K 9/00* (2022.01)
*G06T 7/73* (2017.01)
(Continued)

(52) U.S. Cl.
CPC ................ *G06T 7/75* (2017.01); *A61B 34/10* (2016.02); *A61B 34/20* (2016.02); *G16H 30/20* (2018.01);
(Continued)

(58) Field of Classification Search
CPC ....................................................... G06F 3/011
See application file for complete search history.

(56) References Cited

U.S. PATENT DOCUMENTS 9,141,937 B2 * 9/2015 Dempski ................ G06Q 10/10
2015/0127340 A1 * 5/2015 Epshteyn ................ G10L 21/00
704/235

(Continued)

FOREIGN PATENT DOCUMENTS

WO   2008008905 A2   1/2008
WO   20140122301 A1  8/2014

OTHER PUBLICATIONS

International Search Report and Written Opinion for corresponding International Application No. PCT/EP2019/065553, dated Sep. 12, 2019. 2 pages.

*Primary Examiner* — Hadi Akhavannik
(74) *Attorney, Agent, or Firm* — Tucker Ellis LLP

(57) ABSTRACT

A computer-implemented medical method of determining the position of an anatomical region of interest of a patient's body is provided. The method includes acquiring finger model data, acquiring finger position data based on the finger model data and based on imaging the at least one finger, acquiring planning image data that describes a planning external surface of the anatomical region of interest, and determining anatomical region position data based on the finger position data and the planning image data, wherein the finger model data describes a user-specific model of the pose which is acquired by imaging the at least one finger when it attains the pose.

14 Claims, 3 Drawing Sheets

(51) Int. Cl.
    *A61B 34/10*      (2016.01)
    *A61B 34/20*      (2016.01)
    *G16H 50/50*      (2018.01)
    *G16H 30/20*      (2018.01)
    *G16H 30/40*      (2018.01)

(52) U.S. Cl.
    CPC ............ *G16H 30/40* (2018.01); *G16H 50/50* (2018.01); *A61B 2034/2055* (2016.02); *G06T 2207/30196* (2013.01)

(56) References Cited

U.S. PATENT DOCUMENTS

| | | | |
|---|---|---|---|
| 2016/0085302 A1* | 3/2016 | Publicover | G02B 27/0172 345/633 |
| 2016/0171744 A1* | 6/2016 | Rhoads | G06F 18/22 345/419 |
| 2016/0191887 A1 | 6/2016 | Casas | |
| 2017/0236037 A1* | 8/2017 | Rhoads | G06F 18/00 382/103 |
| 2018/0078331 A1 | 3/2018 | Schaewe | |

\* cited by examiner

REGISTRATION OF AN ANATOMICAL BODY PART BY DETECTING A FINGER POSE

RELATED APPLICATION DATA

This application is a national phase application of International Application No. PCT/EP2019/065553 filed Jun. 13, 2019, which claims priority to International Application No. PCT/EP2018/065746 filed on Jun. 14, 2018, the contents of both of which are incorporated herein by reference.

FIELD OF THE INVENTION

The present invention relates to a computer-implemented method of determining the position of an anatomical region of interest of a patient's body, a corresponding computer program, a non-transitory program storage medium storing such a program and a computer for executing the program, as well as a medical system comprising an electronic data storage device and the afore-mentioned computer.

TECHNICAL BACKGROUND

In the state of the art, the surface of a rigid anatomical structure such as a skin surface on the skull is determined in the planning dataset. Alternatively or additionally anatomical landmarks are identified in the planning dataset. A pointer which is tracked by a 3D localization system (such as an NDI camera) digitizes surface points on the rigid structure or the anatomical position of the aforementioned landmarks. Surface matching algorithms, paired point or hybrid algorithms find a resulting registration between patient and dataset.

The present invention has the object of determining the position and orientation of an anatomical region of interest which may comprise a rigid structure such as a bone or skull need, so that a match (a registration) between the real patient anatomy and their dataset (e.g. magnetic resonance images) can be established. This supports accurate navigation in pre-operative image data.

WO 2014/122301 A1 discloses a method of generating a point cloud-based surface mash of an anatomical surface by detecting a tool or a human hand pointing towards the position of the points in the point cloud in a tracking image of the tool or hand, respectively.

US 2018/078316 A1 discloses a system using images of a subject assist in visualization of hidden portions of the subject which is configured to display images in an augmented or mixed reality manner.

US 2016/0191887 A1 discloses a real-time surgery method and apparatus for displaying a stereoscopic augmented view of a patient from a static or dynamic viewpoint of the surgeon which employs real-time three-dimensional surface reconstruction for preoperative and intraoperative image registration. Stereoscopic cameras provide real-time images of the scene including the patient. A stereoscopic video display is used by the surgeon, who sees a graphical representation of the preoperative or intraoperative images blended with the video images in a stereoscopic manner through a see-through display.

The present invention can be used for navigation procedures e.g. in connection with a system for neorosurgery or spinal surgery such as Cranial Navigation System or Spinal Navigation Application products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses generating or at least acquiring a pose model of a user's hand (hereinforth embodied by finger model data) and determining, from a camera image, the position of the hand (hereinforth embodied by finger position data) when it is placed in a desired position relative to, for example onto, an anatomical region of interest by extracting the part of the image representing the hand from the camera image based on the knowledge of the appearance of the hand gained from the pose model. The position of the hand thus determined is used as an indicator for the position of the anatomical region of interest for example relative to the position of the camera. The pose of the hand when it is placed relative to the anatomical region of interest is used as an indicator for the surface geometry of the anatomical region of interest, and a patient image dataset (hereinforth embodied by planning image data) can then be searched for a similar surface. This similar surface can then be registered to the patient coordinate system based on knowledge of the coordinate system in which positions are defined for the patient image dataset and knowledge of the position of the anatomical region of interest relative to the position of the camera. The resulting registration is hereinforth embodied by anatomical region position data.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining the position of an anatomical region of interest of a patient's body. The region of interest in one example is a surface of an anatomical body part, for example an external surface of anatomical body part. The anatomical body part is for example an external anatomical body part such as a part of the outer layer of the epidermis of the patient or his eyes, or the skin on the skull and/or face. However, the anatomical body part may also be any other body part.

The method comprises executing, on at least one processor of at least one computer (for example at least one computer being part of the navigation system), the following exemplary steps which are executed by the at least one processor.

In a (for example first) exemplary step, finger model data is acquired which describes at least one model (for example, a polygon model, basic kinematic model, or complex kinematic model) of a pose (for example, a predetermined pose) of at least one finger (in examples, a plurality of fingers, the palm of the hand or the whole hand) or at least part of at least one finger (for example the fingertip of the at least one finger or the fingertips of a plurality of fingers) of a user. In a case of a pose of a plurality of fingers, all of the plurality of fingers may be located on the same hand of a user or on different hands of the user. In one example, the finger model data is acquired by imaging the at least one finger when it attains the pose. This allows for example to generate a user-specific model which is generated individually for the user. Alternatively or additionally, the finger model data is acquired for example from atlas data describing a statistically generated image-based model of the at least one finger generated from medical image data taken from a plurality of subjects such as human subjects, for example at least one of healthy persons or patients or users, for example physicians (such as surgeons). The model described by the atlas data may in examples be at least one of a standard patient model, generalized patient model, average patient model, or average human anatomy model.

In one example of the disclosed method, the model of the pose of the at least one finger of one or more users (within this disclosure also termed "finger model") is shared (i.e. made available to a plurality of users) during the registration procedure in a multi-user environment. For example, more such models from different perspectives are acquired according to a specification of this example. In a single-user environment, the model is recorded from the point of view of that single user with limited variations for the distance from the camera to the user's finger. A multi-user environment allows acquiring multiple images of the same pose at the same time at different perspectives. This improves and accelerates registration.

In another example in which a camera tracks the patient via a reference location on the patient or having a predetermined spatial relationship (for example, at least one of position or orientation) to the patient's body, another advantage may arise. The reference location may be defined by the position of a marker device attached to the patient. Here, an image containing pose information defining the model may be used even if the reference location is not visible in the image. In the following, an algorithmic description of that example is offered:

1. A finger pose is extracted from the image without using a reference location (pose A).
2. A finger pose is extracted from the image using a reference location (pose B). The finger pose can be brought into relation to the patient's body.
3. Pose A is brought into relation to pose B and additional pose information is then calculated.
4. With Pose B being in relation to the patient, the additional information from step 3 can be used for registration.

The finger model is in one example acquired using images from more than one user so that a finger model can be acquired from more datasets and/or faster.

In a (for example second) exemplary step, finger position data is acquired based on the finger model data and based on imaging the at least one finger. The finger position data describes a position of the at least one finger (for example, at least part of the at least one finger such as for example only the fingertip of the at least one finger or only the fingertips of a plurality of fingers) when there is a predetermined relative position between the at least one finger and the anatomical region of interest. For example, the finger position data is defined as a point cloud describing points representing positions in three-dimensional space corresponding to at least one fingertip or other parts of the user's hand, for example from a plurality of camera images or from a single image. For example, the finger position data is acquired by extracting, from a camera image generated by the imaging and describing the at least one finger and based on the finger model data (for example by image comparison between the model and the camera image), the position of the image representation of at least part of the at least one finger. For example, the finger position data is determined by extracting the position of the at least one finger from a digital image (such as a camera image) generated using for example a camera for imaging the at least one finger. The position of the at least one finger can be extracted for example by comparing the camera image to the model of the at least one finger. For example, the camera image shows the at least one finger in at least substantially the same pose as the pose of the at least one finger for which the model was generated or a pose which is similar to the pose of the at least one finger for which the model was generated at least to a predetermined degree of similarity. The model and the camera image may then be compared to one another to extract, from the camera image, an image representation of the at least one finger by searching the camera image for contents which is similar to the model of the at least one finger at least to a predetermined degree of similarity, and selecting such contents, if present in the camera image, as the image representation of the at least one finger in the camera image.

In one example, the predetermined relative position between the at least one finger and the anatomical region of interest is position at which the at least one finger at least substantially touches the anatomical region of interest. Alternatively or additionally, the predetermined relative position between the at least one finger and the anatomical region of interest is for example a position at which the at least one finger at least substantially points at the anatomical region of interest and does not touch the anatomical region of interest. This application is similar to using the at least one finger as a pointer for pointing at the anatomical region interest so as to notify for example a medical navigation system of the position of the anatomical region of interest.

In a (for example third) exemplary step, planning image data is acquired which describes a planning external surface of the anatomical region of interest, for example the geometry of the planning external surface. In examples, the planning image data is acquired from medical image data which is defined in two dimensions (for example from at least one radiography, e.g. from merging multiple radiographies having different imaging planes) or three dimensions for example, by applying a tomographic modality such as computed x-ray tomography, magnetic resonance tomography or sonography. In examples, the planning image data is acquired automatically (e.g. by image comparison between a surface or surfaces extracted from the camera image and medical image data describing an anatomical body part comprising the anatomical region of interest) or based on user input (e.g. by manual selection from medical image data, or by voice control). The planning external surface may be determined from the planning image data for example by excluding any potentially relevant surface described by the planning image data which does not fit the (for example, into the) point cloud described by the finger position data.

In a (for example fourth) exemplary step, anatomical region position data is determined based on the finger position data and the planning image data, wherein the anatomical region position data describes the position of the anatomical region of interest. Because the finger position data is acquired based on the finger model data, the anatomical region position data is therefore also determined based on the finger model data. The output of this step is for example a transformation matrix between the reference system used to define positional information defining the planning image data and the below-described procedure reference system. For example, the anatomical region position data is determined by determining, based on the finger position data, an actual surface (for example the geometry of an actual surface) of the anatomical region of interest and comparing the actual external surface (for example the geometry of the actual external surface) to the planning external surface (for example the geometry of the planning external surface). In an example, the actual surface is determined by generating or represented by a point cloud (for example, a three-dimensional point cloud, i.e. a point cloud the positions of which are defined in three dimensions) of positions of the at least one finger. For example, the actual external surface is determined to be the planning external surface if the comparison between the actual external surface and the planning external surface results in that the actual external surface is similar to the planning external surface at least to a predetermined degree of similarity.

For example, the position of the anatomical region determined in the for example fourth exemplary step is a relative position between the anatomical region of interest and a camera used to image the at least one finger and to generate the finger position data, wherein camera position data is acquired which describes the position of an imaging device such as the camera or in a procedure reference system (which is acquired for example by tracking such as optical tracking, by a stereoscopic camera, of a marker array attached to the camera or imaging the camera by a camera included in navigated augmented reality glasses) usable for navigating a medical procedure. For example, the anatomical region procedure position data is determined based on the anatomical region position data and the camera position data. The anatomical region procedure position data describes a position of the anatomical region of interest which is defined for example in the procedure reference system. The procedure reference system is a reference system used to define positions of entities such as an anatomical body part, the anatomical region of interest, or at least one instrument which may be present during conduct of a medical procedure. For example, the procedure reference system is a patient reference system, i.e. a reference system which is patient-centred. The position of the anatomical region of interest in the procedure reference system can be determined by transforming (i.e. mapping) the position of the anatomical region of interest relative to the camera into the procedure reference system on the basis of the position of the camera in the procedure reference system. This can be computed using known algebra.

In one example of the method according to the first aspect, surface scan data is acquired which describes a point cloud of positions of parts of the anatomical region of interest, wherein the surface scan data has been generated using a surface scan device (such as a navigated laser pointer, navigated contact pointer, or navigated surface camera or navigated comparable device such as a range camera, depth camera, stereo camera, time of flight camera, laser scanner, LIDAR, or RGB-Z camera) for scanning the anatomical region of interest (for example, a surface such as an external surface of the anatomical region of interest). Scanning within the meaning of this use is meant to acquire information about the actual position of parts of the anatomical region of interest. Surface subset data is then determined based on the finger position data and the surface scan data, wherein the surface subset data describes a subset (such as a real or strict subset) of the point cloud of positions of the anatomic region of interest. This results in an excision of parts of the scanned surface from the point cloud. Then, the anatomical region position data is determined for example based on the surface subset data and the planning image data. This results in a registration of the excision from the surface scan with planning image which allows for an increase in precision for determining the position of the anatomical region of interest in the procedure reference system, for example compared to the case in which no surface scan data is acquired.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical navigation system, comprising:
 a) the at least one computer according to the fourth aspect;
 b) at least one electronic data storage device storing at least the planning image data and for example the finger model data; and
 c) an imaging device (e.g. the camera) for imaging the at least one finger,
   wherein the at least one computer is operably coupled to
   the at least one electronic data storage device for acquiring, from the at least one data storage device, at least the planning image data and for example the finger model data, and
   the imaging device for acquiring, from the imaging device, at least one signal usable for generating the finger position data.

In a sixth aspect, the invention is directed to use of the system according to the fifth aspect for conducting a medical procedure, wherein the use comprises execution of the steps of the method according to the first aspect for determining the position of the anatomical region of interest.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of executing surgery for making the anatomical region of interest accessible specifically so as to allow the at least one finger to attain the predetermined relative position between the at least one finger and the anatomical region of interest. More particularly, the invention does not involve or in particular comprise or encompass any surgical or therapeutic activity. The invention is instead directed as applicable to determining the position of an anatomical region of interest. For this reason alone, no surgical or therapeutic activity and in particular no surgical or therapeutic step is necessitated or implied by carrying out the invention.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

Atlas data describes (for example defines, more particularly represents and/or is) for example a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
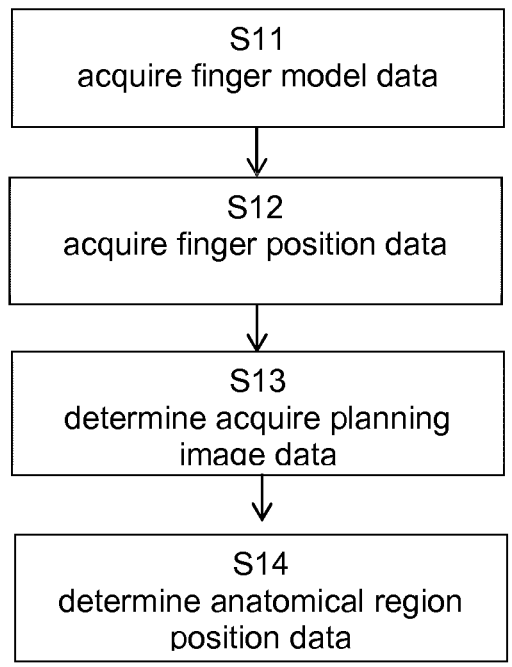
FIG. 1 is a flow diagram illustrating the basic steps of the method according to the first aspect.

FIG. 1 illustrates the basic steps of the method according to the first aspect, in which step S11 encompasses acquisition of the finger model data, step S12 encompasses acquisition of the finger position data on the basis of the finger model data and subsequent step S13 encompasses acquisition of the planning image data. The last step S14 involves determination of the anatomical region position data with the finger position data and the planning image data as input data.

Figure 2:
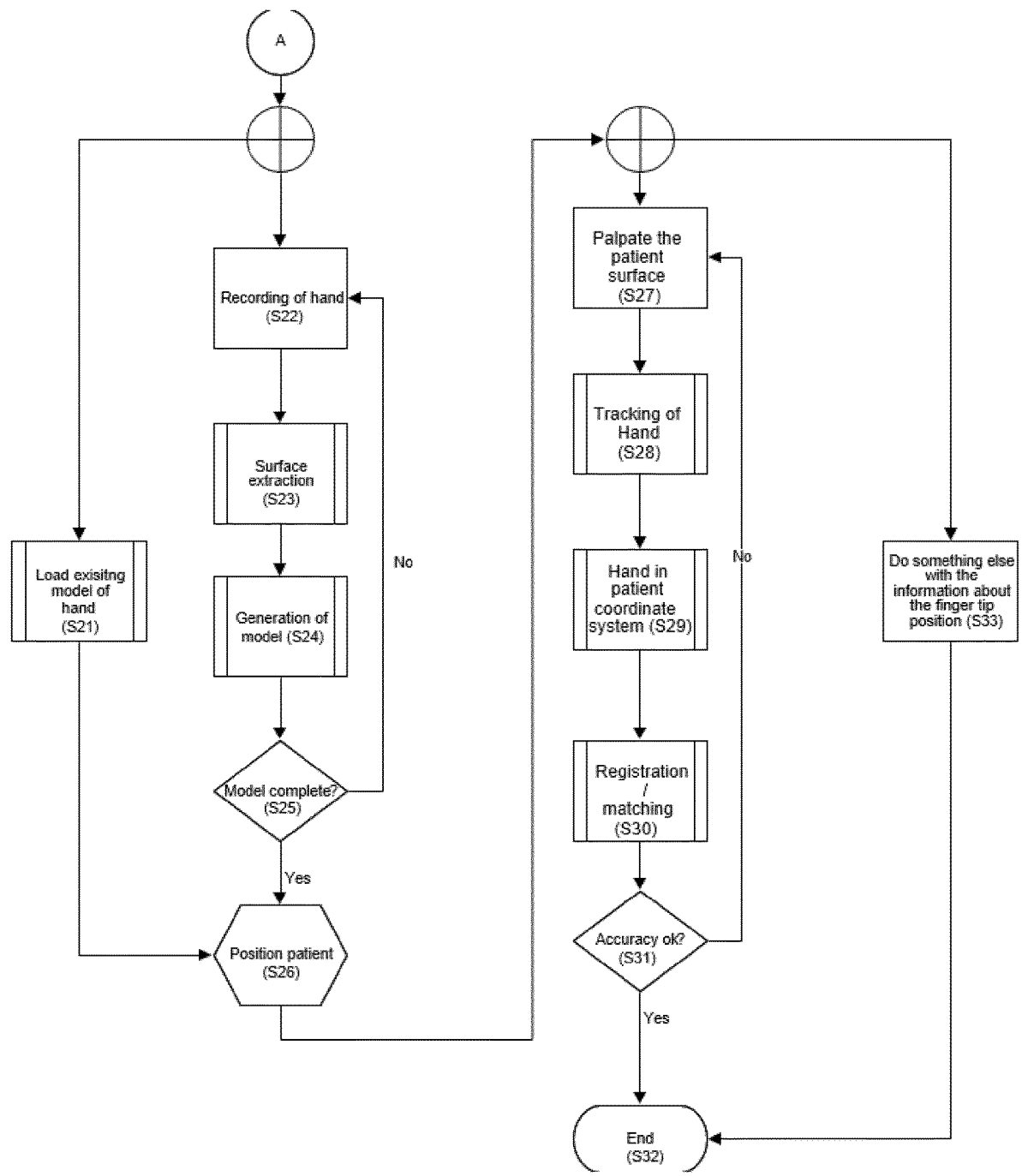
FIG. 2 shows an example of the method according to the first aspect.
Figure 3:
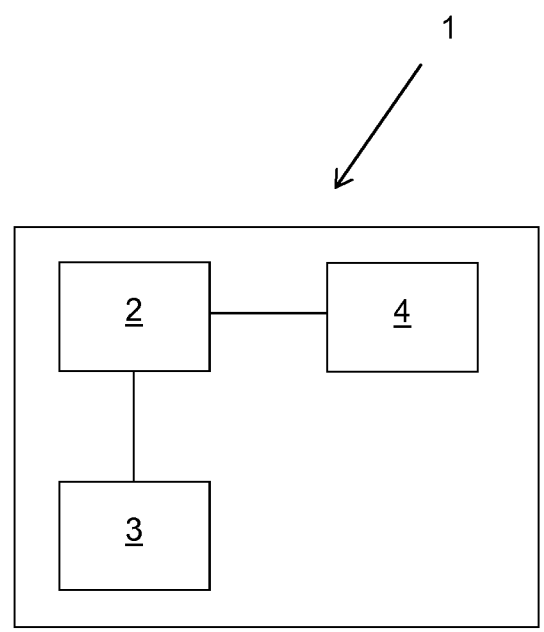
FIG. 3 is a schematic illustration of the system according to the fifth aspect.

FIG. 2 illustrates an example of the method according to the first aspect. Execution of this example starts at step A, and for generating the input for the finger model data, there are two alternatives: Either, an existing (predetermined) model of the hand is read in step S21 (which may be immediately followed by the step of positioning the patient in step S26), or, according to steps S22 to S25, the surface of a user's such as a physician's hand is detected by a camera system and a model of the hand is created. The term of camera denotes a video camera (stereo camera or a single camera). The camera can be part of a head-mounted display such as augmented reality glasses. In step S22, the camera records images of the hand. A camera or a set of cameras (within the framework of this disclosure, both cases are called camera) detects the surface and shape of the hands and fingers of the surgeon. The hands are shown to the camera from different angles. This depends on the requirements of the surface extraction. The user shows his hands to the camera and moves/rotates them until the model can be created. The output data type of this step may be video images (mono or stereo). The surface is then extracted in step S23 by stereo reconstruction (disparity map, topographic map), 3D from motion (continuous tracking), also possible would be a dedicated glove worn on the user's hand with structures on it to facilitate surface reconstruction. Such a structure can also help better tracking of the hand, initialize tracking, or improve tracking of the hand when other features like fingers are currently not visible. To extract the surface neither camera nor the hand need to be tracked. The output data type of this step is at least one of a 3D point cloud, tessellation of surface, disparity map (depending on the actual implementation). From the surface extraction, a model of the hand can be created in step S24. The model comprises different poses of the fingers. This can be obtained by extracting the surface with the hand with the fingers at different positions (clenching hand to first or spreading fingers). It is also possible to have an additional kinematic model of a hand. This can be used to interpolated exact finger positions, for hand movements which have not been recorded. The output data type of this step may be one of the following:

a) polygon model of the hand and finger phalanges (incl. finger thickness);
b) basic kinematic model of the hand based on extracted surfaces from different poses of the hand (spreading fingers, bending fingers); and
c) complex kinematic model of the hand based on extracted surfaces from different poses of the hand. This model could interpolate phalange position, which were not actually recorded.

The model can be stored so that a surgeon has to be acquired only once.

The model of the hands is created and stored. The model can be improved by applying kinematic models of hand/finger movement or by actually recording finger movement. This way the fingertip position can be estimated even though only the proximal and/or intermediate phalange bones are visible.

Step S25 determines whether the model has been completely generated. If it is determined that this is not the case ("no"), then the method repeated from execution of step S22. If the answer to step S25 is "yes", then the patient is positioned in step S26.

Then the user's hand touches, in step S27 the surface of the rigid structure to be registered, while the camera observes the hand. Here the surgeon touches the surface of the patient. For neurosurgery this can be the skin surface (which corresponds with sufficient accuracy to the bone surface). The surgeon then touches the surface of the rigid anatomical structure to be registered. The hands must be visible to the camera during the registration procedure. From model knowledge, the actual position of the finger tips or inside of the hand can be calculated by analyzing the camera image of the back of the hand.

It is not necessary to know whether a hand actually touches the patient. The system would continuously record the camera image. Everywhere where there is a hand, there cannot be patient. By continuously moving and recording the hands, the system limits the patient volume until the dataset can be fitted/registered to required accuracy.

Step S27 is followed by step S28 which involves tracking the user's hand. During registration the hand is recorded by the camera. Based on the model of the hand and the images recorded during registration the hand can be placed into coordinate space of the camera. From model knowledge, the extent of the whole hand can be calculated. When e.g. the back of a finger is seen, the hand/finger position can be determined and as the whole 3D model of the hand is known also the position of the fingertip is known. Finger phalanges do not move independently, so with a recorded position of three phalanges, it is sufficient to know the position of the proximal two, in order to calculate the position of the third (and hence the position of the tip). This would make it possible to track partly hidden fingers.

The system calculates the surface touched by the surgeon during registration. The corresponding surface from preoperative imaging is matched to this surface, hence a registration between patient and their medical imaging data is established.

For registration, the relative location of the camera to the patient is known. This can be achieved by recognizing a marker/structure fixed to the patient, other sensors on the camera (inertia, gravity, etc.) or by tracking the camera with a localizing system (NDI camera e.g.).

Step S29 is directed to determining the position of the position of the hand in the procedure reference system, i.e. the patient coordinate system (patient coordinate space). To place the hand into coordinate space of the patient there are several methods:
1. sensors track the camera and the patient is fixed;
2. sensors track the camera and the patient;
3. the camera tracks the patient via a reference location on the patient (or hardware affixed to the patient).

With the patient reference array (i.e. a marker device attached to the patient's body) visible in the images, the hand can also be placed relative to the patient coordinate space.

The surface defined by the hand in the camera images is then registered/matched in step S30 to the planning image data. For registration the relative location of the camera to the patient is known. This can be achieved by recognizing a marker/structure fixed to the patient, other sensors on the camera (inertia, gravity, etc.) or by a tracking the camera with a localizing system (NDI camera e.g.). If the camera is installed in a fixed position and the patient is not moving, a tracking of the camera may not be necessary and it is sufficient to detect the hands in the camera images. From the multitude of hand positions in patient space (and information about orientation of the palm) a surface or non-patient volume can be created. The surface extracted from the planning image data (patient dataset such as e.g. MRI, CT) can be matched to the surface extracted from the camera image, and a parameter for matching quality can be calculated to determine the accuracy of registration (see infra concerning the description of step S31). The output of this step is a transformation matrix between the reference system used to define positional information defining the planning image data and the patient coordinate system.

S31 involves checking the accuracy of the registration. If the accuracy is satisfactory ("yes"), the method ends in step S32. If the accuracy is not satisfactory ("no"), execution of the method is repeated from step S27.

Instead of steps S27 to step S31 (i.e. instead of registering the patient surface with the planning image data), something else may be done with the information about the position of the hand or at least one fingertip. For example, this information may be used to do at least one of the following:
navigate, for example by using the hand or fingertip as a pointer;
extract surface;
control user interface (use your finger to touch a virtual touch screen);
tap with the finger on an instrument to mimic button press; or
gesture recognition, e.g. for controlling the navigation system.

FIG. 6 is a schematic illustration of the medical navigation system 1 according to the fifth aspect. The system is in its entirety identified by reference sign 1 and comprises a computer 2, an electronic data storage device (such as a hard disc) 3 for storing at least the planning image data and an imaging device 4 (such as a stereoscopic camera or a camera included in navigated augmented reality glasses). The components of the medical system 1 have the functionalities and properties explained above with regard to the fifth aspect of this disclosure.

The invention claimed is:

1. A computer-implemented method of determining a position of an anatomical region of interest of a patient's body, the method comprising:

a) acquiring finger model data which describes at least one model of a pose of at least one finger of a user;
b) acquiring finger position data based on the finger model data and based on imaging the at least one finger, wherein the finger position data describes a position of the at least one finger at which the at least one finger points at the anatomical region of interest and wherein the finger position data is acquired by extracting, from a camera image generated by the imaging and describing the at least one finger, a position of an image representation of at least part of the at least one finger by comparing the camera image to the model of the at least one finger;
c) acquiring planning image data which describes a planning external surface of the anatomical region of interest; and
d) determining anatomical region position data based on the finger position data and the planning image data, wherein the anatomical region position data describes the position of the anatomical region of interest, wherein the anatomical region position data is determined by determining, based on the finger position data, an actual external surface of the anatomical region of interest and comparing the actual external surface to the planning external surface, wherein the actual external surface is determined by generating or represented by a point cloud of positions of the at least one finger, wherein the actual external surface is determined to be the planning external surface if the comparison between the actual external surface and the planning external surface results in that the actual external surface is similar to the planning external surface at least to a predetermined degree of similarity,
wherein the finger model data describes a user-specific model of the pose.

2. The method according claim 1, comprising:
acquiring surface scan data which describes a point cloud of positions of parts of the anatomical region of interest, wherein the surface scan data has been generated using a surface scan device for scanning the anatomical region of interest; and
determining surface subset data based on the finger position data and the surface scan data, wherein the surface subset data describes a subset of the point cloud of positions of the anatomic region of interest,
wherein the anatomical region position data is determined based on the surface subset data and the planning image data.

3. The method according to claim 1, wherein the position described by the finger position data is a position at which the at least one finger touches the anatomical region of interest.

4. The method according to claim 1, wherein the position of the anatomical region is a relative position between the anatomical region of interest and a camera used to image the at least one finger and to generate the finger position data, wherein camera position data is acquired which describes the position of the camera in a procedure reference system usable for navigating a medical procedure, and wherein anatomical region procedure position data is determined based on the anatomical region position data and the camera position data, wherein the anatomical region procedure position data describes a position of the anatomical region of interest in the procedure reference system.

5. The method according to claim 1, wherein the finger model data is acquired from atlas data describing a statistically generated image-based model of the at least one finger generated from medical image data taken from a plurality of subjects.

6. The method according to claim 1, wherein the planning image data is acquired automatically or based on user input.

7. The method according to claim 1, wherein the model of a pose of at least one finger of the user is made available to a plurality of users, and wherein the finger position data is generated from points of view of the plurality of users.

8. The method according to claim 1, wherein the finger position data is extracted from a camera image using a reference location having a predetermined spatial relationship to the patient's body.

9. A program logic stored in a memory device of a computer that, when executed by the computer or when loaded onto the computer, causes the computer to perform a method of determining a position of an anatomical region of interest of a patient's body, the method comprising:
    acquiring finger model data which describes at least one model of a pose of at least one finger of a user;
    acquiring finger position data based on the finger model data and based on imaging the at least one finger, wherein the finger position data describes a position of the at least one finger at which the at least one finger points at the anatomical region of interest and wherein the finger position data is acquired by extracting, from a camera image generated by the imaging and describing the at least one finger, a position of an image representation of at least part of the at least one finger by comparing the camera image to the model of the at least one finger;
    acquiring planning image data which describes a planning external surface of the anatomical region of interest; and
    determining anatomical region position data based on the finger position data and the planning image data, wherein the anatomical region position data describes the position of the anatomical region of interest, wherein the anatomical region position data is determined by determining, based on the finger position data, an actual external surface of the anatomical region of interest and comparing the actual external surface to the planning external surface, wherein the actual external surface is determined by generating or represented by a point cloud of positions of the at least one finger, wherein the actual external surface is determined to be the planning external surface if the comparison between the actual external surface and the planning external surface results in that the actual external surface is similar to the planning external surface at least to a predetermined degree of similarity,
    wherein the finger model data describes a user-specific model of the pose.

10. A medical navigation system, comprising:
    a) at least one computer configured to perform a method including:
        acquiring finger model data which describes at least one model of a pose of at least one finger of a user;
        acquiring finger position data based on the finger model data and based on imaging the at least one finger, wherein the finger position data describes a position of the at least one finger at which the at least one finger points at an anatomical region of interest and wherein the finger position data is acquired by extracting, from a camera image generated by the imaging and describing the at least one finger, a position of an image representation of at least part of the at least one finger by comparing the camera image to the model of the at least one finger;
        acquiring planning image data which describes a planning external surface of the anatomical region of interest; and
        determining anatomical region position data based on the finger position data and the planning image data, wherein the anatomical region position data describes the position of the anatomical region of interest, wherein the anatomical region position data is determined by determining, based on the finger position data, an actual external surface of the anatomical region of interest and comparing the actual external surface to the planning external surface, wherein the actual external surface is determined by generating or represented by a point cloud of positions of the at least one finger, wherein the actual external surface is determined to be the planning external surface if the comparison between the actual external surface and the planning external surface results in that the actual external surface is similar to the planning external surface at least to a predetermined degree of similarity,
        wherein the finger model data describes a user-specific model of the pose;
    b) at least one electronic data storage device storing planning image data; and
    c) an imaging device for imaging the at least one finger, wherein the at least one computer is operably coupled to
        the at least one electronic data storage device for acquiring, from the at least one electronic data storage device, at least the planning image data, and
        the imaging device for acquiring, from the imaging device, at least one signal usable for generating the finger position data.

11. The medical navigation system according to claim 10, wherein the at least one electronic data storage device stores the finger model data.

12. The method according to claim 1, wherein the user-specific model of the pose is acquired by imaging the at least one finger when it attains the pose.

13. The program logic of claim 9, wherein the user-specific model of the pose is acquired by imaging the at least one finger when it attains the pose.

14. The medical navigation system of claim 10, wherein the user-specific model of the pose is acquired by imaging the at least one finger when it attains the pose.

* * * * *